United States Patent [19]

Martin et al.

[11] 4,032,548

[45] June 28, 1977

[54] PROCESS FOR PREPARING 1,4-NAPHTHOQUINONE

[75] Inventors: Manfred Martin, Cologne; Gerhard Scharfe, Leverkusen, both of Germany

[73] Assignee: Bayer Aktiengesellschaft, Leverkusen, Germany

[22] Filed: July 9, 1975

[21] Appl. No.: 594,486

[30] Foreign Application Priority Data

Aug. 2, 1974 Germany .......................... 2437221

[52] U.S. Cl. ........................... 260/396 R; 252/416; 260/346.4
[51] Int. Cl.² ......................................... C07C 49/66
[58] Field of Search ..................... 260/396 R, 346.4

[56] References Cited
UNITED STATES PATENTS 2,765,323  10/1956  Dixon et al. .................. 260/396 R
3,095,430  6/1963  Wittstein ....................... 260/396 R
3,232,955  2/1966  Nonnenmacher et al. .... 260/396 R
3,402,187  9/1968  Kaiser et al. .................. 260/396 R Primary Examiner—Vivian Garner
Attorney, Agent, or Firm—Burgess, Dinklage & Sprung

[57] ABSTRACT

1,4-Naphthoquinone is prepared by reacting naphthalene with molecular oxygen in a gaseous phase in the presence of a catalyst containing vanadium. Prior to reacting the naphthalene with oxygen, the catalyst is pre-treated with molecular oxygen at 300° to 400° C in the absence of organic compounds and immediately thereafter a gas mixture containing naphthalene and molecular oxygen is passed over the pretreated catalyst at temperatures in the range of 300° to 400° C. The catalyst pre-treatment can be carried out in the presence of water vapor and the subsequent reaction of naphthalene with molecular oxygen can also be carried out in the presence of water vapor.

2 Claims, No Drawings

PROCESS FOR PREPARING 1,4-NAPHTHOQUINONE

BACKGROUND

The present invention relates to a process for the preparation of 1,4-naphthoquinone — hereafter referred to, for brevity, as naphthoquinone — by reaction of naphthalene with molecular oxygen in the gas phase in the presence of a catalyst containing vanadium.

Naphthoquinone is a valuable intermediate product for the preparation of anthraquinone (see German Published Application 2,218,316).

It is known from Belgian Patent 798,181 to react naphthalene in the gas phase with molecular oxygen in the presence of a catalyst containing vanadium, to give naphthoquinone and phthalic anhydride. It is also known, from the same patent specification, to carry out the reaction of naphthalene to naphthoquinone by passing a gas mixture consisting essentially of nitrogen, oxygen, water vapour, carbon dioxide and naphthalene under pressure at elevated temperature through a reactor in which a catalyst, containing vanadium, is located in reaction tubes arranged in parallel.

SUMMARY

According to the present invention, there is provided a process for the manufacture of naphthoquinone by reaction of naphthalene with molecular oxygen in the gas phase in the presence of a catalyst containing vanadium, which is characterised in that, before the reaction of the naphthalene with oxygen, the catalyst is treated with molecular oxygen at 300° to 400° in the absence of organic compounds and immediately thereafter a gas mixture containing naphthalene and molecular oxygen is passed over the catalyst at a temperature of from 300° to 400° C.

A preferred embodiment of the process according to the invention is to carry out the pretreatment of the catalyst with molecular oxygen in the absence of organic compounds at 300° to 400° C in the presence of water vapor. It is furthermore advantageous to carry out the subsequent reaction of naphthalene with molecular oxygen at 300° to 400° C in the presence of water vapour.

DESCRIPTION

The preparation of naphthoquinone by reaction of naphthalene with molecular oxygen in the gas phase in the presence of a catalyst containing vanadium is in itself known. In a particularly advantageous embodiment of the process, the procedure followed is that a gas mixture consisting essentially of nitrogen, oxygen, water vapor, carbon dioxide and naphthalene is passed under pressure at elevated temperature through a reactor in which the catalyst containing vanadium is located in reaction tubes arranged in parallel. Suitable working conditions for this are, for example, 3 - 8 atmospheres, 300° to 400° C, and input concentrations of 1 to 5 mol % of naphthalene, 5 to 15 mol % of water, 1 - 15 mol % of carbon dioxide and 1 - 10 mol % of oxygen.

The naphthalene employed can be either pure or in its commercially available forms, for example as petronaphthalene or coal tar naphthalene, which can contain impurities such as methylnaphthalene and sulphur compounds such as thionaphthalene. The catalysts containing vanadium which are used are also known. Their manufacture is described, for example, in Fiat Report 649, London, 1947, pages 2 and 3. The catalysts used can contain, as additional components, compounds of silicon, aluminium or titanium, for example in the form of the oxides.

Examples of further additives which are known are the salts of the alkali metals and alkaline earth metals; alkali metal sulphates, alkali metal phosphates and alkali metal borates may be mentioned in this context. In a particular embodiment of the process, a catalyst which contains vanadium oxide, silica and potassium sulphates, for example in the form of potassium disulphate, is used.

The process of preparation according to Fiat Report 649, London, 1947, pages 2 to 3, can be modified in a great variety of ways, for example by varying the pH value during the preparation of the catalyst, varying the drying conditions, selecting certain particle sizes when grinding the dried material which is obtained in the individual stages of preparation of the catalyst, adding substances which decompose on drying or calcining, such as ammonium carbonate, or using additives, such as graphite, in order to obtain the desired strength when molding the catalyst mass to form tablets or spheres. The finished catalyst can furthermore be modified by drying or calcining, for example at temperatures of 200° to 500° C.

The pretreatment, according to the invention, of the catalyst is in general carried out with molecular oxygen in the absence of organic compounds at 300° to 400° C, preferably at 330° to 370° C. It can be carried out under normal pressure but also under elevated pressure, for example at pressures of 3 to 8 bars, preferably of 5 to 7 bars. The pretreatment can be carried out either with pure molecular oxygen or with nitrogen-oxygen mixtures. Where nitrogen-oxygen mixtures are used, these can be air or mixtures which, for example, contain from 5 to 10% by volume of oxygen. The absence of organic compounds is ensured in a manner which is in itself known, for example by using industrial gases such as oxygen, nitrogen, or air which are free from organic compounds. When carrying out the pretreatment industrially, complete absence of organic compounds can under certain circumstances not always be achieved entirely, but it is desirable that the process should be carried out to a great extent entirely in the absence of organic compounds such as, for example, naphthalene. In general, however, it suffices if the content of organic compounds is less than 100 mg of carbon per cubic meter at standard temperature and pressure.

In a particularly preferred procedure, water vapor, in general in an amount of 5 to 15, preferably 8 to 12% by volume, is added to the gas or gas mixture employed for the pretreatment.

The duration of the pretreatment can vary within wide limits, for example between 1 and 50 hours. However it is also possible, should this appear advantageous for technical reasons, to use longer pretreatment times, for example between 50 and 200 hours. It can be advantageous, before passing the gas mixture containing oxygen and naphthalene over the pretreated catalyst, to adjust the temperature from the pretreatment temperature to the subsequent reaction temperature within the range from 300° to 400° C. For example, the pretreatment can be carried out for a period of 24 hours at 350° C, the temperature can then be set to 320° C and the gas mixture containing naphthalene and oxygen can then be passed over the pretreated catalyst at this temperature of 320° C in order to carry out the reaction to naphthoquinone. The temperature can then be varied further and be adjusted within a certain period to the optimum reaction temperature, for example to 360° C, in the course of, for example, 24 hours. In a preferred embodiment of the process, the reaction of naphthalene with oxygen is carried out, after conclusion of the pretreatment, at 300°-400° C under pressure.

In reacting naphthalene and oxygen in the gas phase in the presence of catalysts containing vanadium, essentially the following three reactions take place:
1. Oxidation of naphthalene to naphthoquinone
2. Oxidation of naphthalene to phthalic anhydride
3. Oxidation of naphthalene to carbon dioxide.

These three main reactions can be illustrated by the following equations:

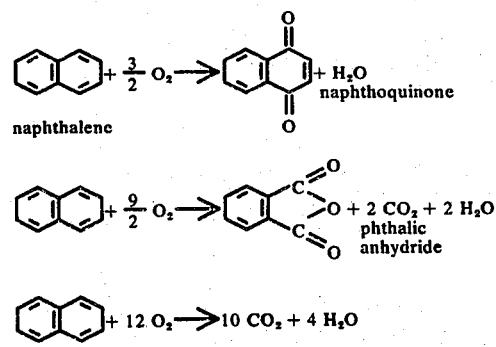

The conversion of naphthalene in general produces a mixture of naphthoquinone and phthalic anhydride, for example in the ratio of 1:2 to 2:1. Since phthalic anhydride is an industrially important intermediate product, for example for the preparation of phthalic acid esters, it can be of advantage, when using the process commercially for the preparation of naphthoquinone and, if relevant, when processing the naphthoquinone further to give anthraquinone, to convert a part of the naphthalene into phthalic anhydride in order simultaneously to prepare, in one plant, two industrially important products, such as phthalic anhydride and naphthoquinone. However, in general it is desirable to direct the conversion of the naphthalene so that preferentially naphthoquinone is produced alongside phthalic anhydride. The third reaction, the oxidation of naphthalene to carbon dioxide and water, is an undesired side-reaction. In industrial operation, all measures by means of which it is possible to keep the extent of this side-reaction low are of interest.

The reaction of naphthalene with oxygen to give naphthoquinone and phthalic anhydride in general starts at 250° C. If the method used is that a gas containing naphthalene and oxygen is passed over the catalyst at 250° C and that the temperature is then slowly raised, for example over a period of 50 hours, in order to arrive at a temperature, for example 360° C, which is optimum with regard to the naphthoquinone yield and selectivity, it is found, surprisingly, that the results which are obtained, for example, after 100, 500 and 1,000 hours, are distinctly less favorable than if the process according to the invention is used. Further disadvantages of the generally customary start-up of the catalyst are an unfavorable axial temperature profile of the catalyst in the reaction tubes and a tendency to spontaneous local temperature rises to above 400° C (run-away of the reactor). In general, this is then associated with damage to the catalyst, in respect to activity and selectivity.

The pretreatment of the catalyst, in accordance with the invention, not only applies to the first start-up of a catalyst, a so-called fresh catalyst, but also to the start-up of a used catalyst. If, for example, a break in operation is necessary for any reason, it is advantageous to change the reactor over to the operating conditions of the pretreatment according to the invention. On longer stoppages it is also possible to cool the catalyst temporarily, for example to temperatures below 200° C, in which case it is then subjected to the pretreatment according to the invention prior to renewed startup. In addition, if the catalyst has been damaged for any reason, for example through temporary exposure to excessive temperatures, it can be regenerated by the process according to the invention and be restored virtually to the original activity and selectivity.

Further advantages of the process according to the invention are that a fresh catalyst can be brought to its full performance, in respect to activity and selectivity, within a very short time, for example in 5 to 10 hours. In addition, catalysts of long working life, such as is desirable and necessary for industrial application of the process, are obtained. Damage to the catalyst due to interruptions in operation, prolonged stoppages, and unfavourable running conditions due to mis-settings, can be reversed by the pretreatment according to the invention.

EXAMPLE 1

The following reaction was carried out in a steel reaction tube of 3 m length and 30 mm internal diameter, heated in a salt bath. 2 liters of a catalyst containing vanadium were introduced into the reactor. The catalyst was prepared in accordance with the preparation instructions given in Fiat Report 649, London, 1947, page 2 to 3. First, a gas mixture of 94% of nitrogen and 6% of oxygen was passed over the catalyst at a rate of 4 $Nm^3$/hour (1 $Nm^3$ = 1 $m^3$ at 1 atm. and 0° C) at room temperature and a pressure of 6 bars. The system was heated to 200° C and water in an amount of 300 ml/hour was then also added. The system was then heated to 350° C and the catalyst was treated with the nitrogen-oxygen-water vapor mixture for 24 hours at this temperature and at 6 bars. The system was then cooled to a temperature of 320° C and gaseous naphthalene in an amount of 690 g/hour was then passed over the catalyst in addition to the mixture containing nitrogen, oxygen and water vapor. Thereafter the temperature was raised to 360° C at a rate of 6°/hour. The following results were obtained over a period in excess of 1,000 hours.

| time in hours | g of naphtho- quinone/ hour | g of phthalic anhydride/ hour | % of reacted naphthalene converted to $CO_2$ |
|---|---|---|---|
| 100 | 96 | 88 | 1 |
| 500 | 94 | 87 | 2 |
| 1,000 | 98 | 90 | 1 |

COMPARISON EXAMPLE

The same apparatus and the same catalyst as in Example 1 were used. 4 $Nm^3$ of a mixture of 94% of nitrogen and 6% of oxygen, and, in addition, 300 ml/hour of water and 690 g of naphthalene were passed hourly over the catalyst as in Example 1 at 6 bars. The temperature was initially set to 250° C for 4 hours. Thereafter the temperature was raised to 360° C over a period of 48 hours. The following results were obtained.

| time in hours | g of naphthoquinone/ hour | g of phthalic anhydride/ hour | % of reacted naphthalene converted to $CO_2$ |
|---|---|---|---|
| 100 | 20 | 24 | 15 |
| 500 | 74 | 80 | 7 |
| 1,000 | 60 | 77 | 8 |

What is claimed is:

1. Process for preparing 1,4-naphthoquinone by reacting naphthalene with molecular oxygen in the gas phase in the presence of a catalyst consisting essentially of vanadium oxide, potassium sulphate and silicic acid which comprises, prior to the reaction of naphthalene with oxygen, treating the catalyst with molecular oxygen at 300 to 400° C in the presence of water vapor and in the absence of organic compounds and immediately thereafter passing a gas mixture consisting essentially of nitrogen, oxygen, water vapor, carbon dioxide and naphthalene over the pretreated catalyst at temperatures of 300° to 400° C and pressures from 3 to 8 atmospheres.

2. Process of claim 1 wherein the naphthalene content is from 1 to 5 mol percent, the water content is from 5 to 15 mol percent and the oxygen content is from 1 to 10 mol percent.

* * * * *